(12) United States Patent
Ssenyange et al.

(10) Patent No.: US 12,138,081 B2
(45) Date of Patent: Nov. 12, 2024

(54) ASTHMA MANAGEMENT SYSTEM AND METHOD

(71) Applicant: CAIRE Diagnostics Inc., Pleasanton, CA (US)

(72) Inventors: Solomon Ssenyange, Fremont, CA (US); Ryan Leard, Oakland, CA (US); David Anvar, Sunnyvale, CA (US); Brian Awabdy, Dublin, CA (US); Todd Smith, Sunnyvale, CA (US); Vivek Balasubramanyam, Pleasanton, CA (US)

(73) Assignee: CAIRE Diagnostics Inc., Pleasanton, CA (US)

( * ) Notice: Subject to any disclaimer, the term of this patent is extended or adjusted under 35 U.S.C. 154(b) by 189 days.

(21) Appl. No.: 16/902,787

(22) Filed: Jun. 16, 2020

(65) Prior Publication Data
US 2020/0390400 A1    Dec. 17, 2020

Related U.S. Application Data

(60) Provisional application No. 62/862,471, filed on Jun. 17, 2019.

(51) Int. Cl.
*A61B 5/0205*    (2006.01)
*A61B 5/00*    (2006.01)
(Continued)

(52) U.S. Cl.
CPC .............. *A61B 5/7275* (2013.01); *A61B 5/08* (2013.01); *A61B 5/7475* (2013.01); *G16H 20/10* (2018.01); *G16H 40/63* (2018.01); *G16H 40/67* (2018.01)

(58) Field of Classification Search
CPC ....... A61B 5/7275; A61B 5/08; A61B 5/7475; G16H 40/67; G16H 20/10; G16H 40/63
See application file for complete search history.

(56) References Cited

U.S. PATENT DOCUMENTS

| | | | | |
|---|---|---|---|---|
| 5,051,903 A | * | 9/1991 | Pelc ................... | G01R 33/5673 324/309 |
| 8,425,428 B2 | * | 4/2013 | Wood ..................... | A61B 5/083 600/538 |

(Continued)

OTHER PUBLICATIONS

Brand et al., Usefulness of monitoring lung function in asthma (Year: 2003).*

(Continued)

*Primary Examiner* — Quang Pham

(57) ABSTRACT

An asthma management system and method are disclosed for collecting environmental and individual health data to predict the onset of asthma symptoms to allow for preventative therapy tailored on an individual basis. In one embodiment a computer system is in electrical communication with an individual user interface and one or more environmental factor collection points via a communications network. The user interface is adapted to send and receive asthma-related data including asthma profile and real-time asthma status data to the computer system via the communication network, and the environmental factor collection points are adapted to send and receive data to the computer system via the communications network. The computer system further comprises one or more processors connected to memory, and are programmed with executable instructions for implementing one or more algorithms for (1) collecting and storing in memory data received from the individual user interface and from the environmental factor collection points, (2) aggregating the data received from the individual user interface and the environmental factor collection points, (Continued)

and (3) implementing one or more algorithms to generate an asthma symptom onset prediction based on the aggregated data. The onset prediction is then communicated to the user interface. In addition, the one or more processors are further programmed with executable instructions to revise one or more asthma symptom onset prediction algorithms where the generated asthma onset prediction and an individual's real-time asthma status data indicate a prediction error.

6 Claims, 3 Drawing Sheets

(51) Int. Cl.
*A61B 5/08* (2006.01)
*G16H 20/10* (2018.01)
*G16H 40/63* (2018.01)
*G16H 40/67* (2018.01)

(56) References Cited

U.S. PATENT DOCUMENTS

| | | | | |
|---|---|---|---|---|
| 9,131,902 | B2* | 9/2015 | Halperin | A61B 5/0823 |
| 9,550,031 | B2* | 1/2017 | Van Sickle | A61M 15/00 |
| 10,004,452 | B2* | 6/2018 | Kazem-Moussavi | A61B 5/742 |
| 10,431,329 | B2* | 10/2019 | Kagen | G16H 70/60 |
| 11,147,505 | B1* | 10/2021 | Shoeb | A61B 5/6801 |
| 2005/0119586 | A1* | 6/2005 | Coyle | A61B 5/1135 600/538 |
| 2005/0192508 | A1* | 9/2005 | Lange | A61B 5/0823 128/920 |
| 2008/0114260 | A1* | 5/2008 | Lange | A61B 5/0823 600/529 |
| 2008/0161657 | A1* | 7/2008 | Bullens | A61B 5/0031 600/301 |
| 2008/0183095 | A1* | 7/2008 | Austin | A61B 5/0809 600/534 |
| 2008/0262381 | A1* | 10/2008 | Kolen | A61B 5/4818 600/595 |
| 2009/0112114 | A1* | 4/2009 | Ayyagari | A61B 7/003 600/529 |
| 2011/0125044 | A1* | 5/2011 | Rhee | A61B 7/003 600/534 |
| 2012/0083670 | A1* | 4/2012 | Rotondo | A61B 5/6814 600/301 |
| 2012/0116241 | A1* | 5/2012 | Shieh | A61B 5/082 600/539 |
| 2012/0271560 | A1* | 10/2012 | Colquitt | A61B 5/0205 702/19 |
| 2013/0072763 | A1* | 3/2013 | Shtalryd | A61B 5/01 600/534 |
| 2015/0242586 | A1* | 8/2015 | Kagen | G16H 10/20 705/2 |
| 2015/0250408 | A1* | 9/2015 | Ssenyange | G01N 33/0016 600/532 |
| 2015/0338390 | A1* | 11/2015 | Anglin, Jr. | G01N 27/227 73/23.3 |
| 2016/0171170 | A1* | 6/2016 | Clifton | A61B 5/7264 703/2 |
| 2016/0224750 | A1* | 8/2016 | Kethman | G16H 40/63 |
| 2016/0228037 | A1* | 8/2016 | Bubis | A61B 5/0816 |
| 2016/0338619 | A1* | 11/2016 | Roxhed | G05D 7/012 |
| 2017/0161453 | A1* | 6/2017 | Stahmann | G16H 20/10 |
| 2017/0325695 | A1* | 11/2017 | Freeman | A61B 5/6823 |
| 2017/0347950 | A1* | 12/2017 | Jones | G08B 21/0461 |
| 2018/0117359 | A1* | 5/2018 | Hale | A61N 5/1037 |
| 2018/0129786 | A1* | 5/2018 | Khine | G16H 40/67 |
| 2018/0177432 | A1* | 6/2018 | Au | A61B 5/7264 |
| 2018/0310861 | A1* | 11/2018 | Kushner | A61B 5/6831 |
| 2018/0322950 | A1* | 11/2018 | Cronin | A61B 5/026 |
| 2018/0344208 | A1* | 12/2018 | Ogasawara | A61B 5/7221 |
| 2019/0102522 | A1* | 4/2019 | Barrett | G16H 10/65 |
| 2019/0167176 | A1* | 6/2019 | Annoni | A61B 5/4035 |
| 2019/0167209 | A1* | 6/2019 | Annoni | A61B 5/0826 |
| 2019/0200937 | A1* | 7/2019 | Mena Benito | G16H 30/20 |
| 2020/0058403 | A1* | 2/2020 | Barrett | G16H 50/20 |
| 2020/0229735 | A1* | 7/2020 | Muchmore | A61B 5/7225 |
| 2020/0297955 | A1* | 9/2020 | Shouldice | G16H 40/67 |
| 2020/0390351 | A1* | 12/2020 | Kesaniemi | A61B 5/7275 |
| 2021/0082582 | A1* | 3/2021 | Barrett | G01W 1/00 |
| 2021/0186368 | A1* | 6/2021 | Kawecki | G08B 27/006 |
| 2021/0219925 | A1* | 7/2021 | Au | A61B 5/1135 |
| 2022/0218290 | A1* | 7/2022 | Zikria | A61B 5/486 |
| 2022/0233093 | A1* | 7/2022 | Zikria | G16H 50/20 |

OTHER PUBLICATIONS

Pijnenburg et al., Monitoring asthma in children (Year: 2015).*
Sly et al., Is home monitoring of lung function worthwhile for children (Year: 2001).*
Miskoff et al., Fractional Exhaled Nitric Oxide Testing Diagnostic Utility in Asthma, Chronic Obstructive Pulmonary Disease, or Asthma chronic Obstructive Pulmonary Disease Overlap Syndrome (Year: 2019).*
Menzies-Gow, Clinical utility of fractional exhaled nitric oxide in severe asthma .management (Year: 2020).*
Alharbi et al., Predictive Models for Personalized Asthma Attacks based on Patient's Biosignals and Environmental Factors: A Systematic Review (Year: 2021).*
Bhat et al., Machine Learning-Based Asthma Risk Prediction Using IoT and Smartphone Applications (Year: 2021).*
Alharbi et al., Asthma Attack Prediction based on Weather Factors (Year: 2019).*

* cited by examiner

ASTHMA MANAGEMENT SYSTEM AND METHOD

CROSS REFERENCE TO RELATED APPLICATIONS

This application claims the benefit of U.S. Provisional Application No. 62/862,471 filed on Jun. 17, 2019, the subject matter of which is herein incorporated by reference in its entirety.

FIELD OF THE INVENTION

The present invention is directed to the management of asthma symptoms, and more particularly to a system for individual management of asthma to inhibit the onset of asthma symptoms in asthma sufferers.

BACKGROUND

Airways carry air into and out of the lungs, and there are a number of diseases that affect the airways of individuals. Examples of such diseases include obstructive pulmonary disease (COPD), bronchiectasis, and asthma. With respect to asthma in particular, the Centers for Disease Control and Prevention (CDC) estimate that about 1 in 12 people in the United States suffer from the disease. This amounts to about twenty-five million asthma sufferers in the U.S., and the number continues to grow. Worldwide, there is an estimated three-hundred million asthma sufferers. In the U.S. alone, the cost attributed to the treatment of asthma is over $50 billion a year. Asthma related deaths are estimated to be over 200,000 annually worldwide.

Asthma is a chronic disease of the airways. In asthma sufferers, the walls of the airways become irritated and swollen, making the airways sensitive to irritants, for example, allergens. In asthma sufferers, irritants, to which an individual is sensitive, cause the airways to narrow. This inflammatory reaction in a hyper-reactive asthma sufferer's airways restricts the flow of air into and out of the lungs. Asthma symptoms include wheezing, coughing, tightness in the chest and shortness of breath. When the symptoms are severe, e.g., an asthma attack, the sufferer may require urgent care. Such attacks can be fatal.

Irritants that cause the onset of asthma symptoms (asthma triggers) are not the same for each person. For one person, a trigger may consist of a single irritant; in others, triggers may comprise a combination of things that act as the trigger. In fact, the range of potential triggers is wide ranging, and includes, for example, such things as dust mite allergens, cockroach allergens and other animal allergens, such as from pets, and other atmospheric particulate matter, including soot, smoke, fly ash, cement dust, suspended atmospheric dust, settling dust, heavy dust, viruses, bacteria, mold spores, pollen, and the like.

Although a person may exhibit asthma symptoms, such as coughing, that person may not have asthma. In order to determine whether an individual has asthma, a number of pulmonary function tests are employed by medical practitioners to diagnose the disease. These tests include, for example, spirometry, lung volume tests, lung diffusion capacity, pulse oximetry and arterial blood gas tests.

In recent years, measurement of exhaled nitric oxide (eNO) has been shown to be a non-invasive and complementary tool to other pulmonary function tests in assessing airway inflammation. This measurement is now a globally accepted biomarker for airway inflammation. Nitric oxide is produced endogenously in cells by NO synthase and secreted by eosinophils in the distal alveoli. Its production is increased in response to inflammatory cytokines (which is associated with asthmatic episodes), and exhaled NO is thought to be an indirect measurement of airway eosinophilic inflammation. Thus, nitric oxide exhaled from the lower airways (e.g., non-nasal airways) can be correlated with the degree of airway inflammation.

As indicated above, it has been found that patients with asthma have high levels of NO in their exhaled breath. Nitric oxide levels increase prior to the presence of clinical symptoms and its levels decline in response to appropriate therapy as airway inflammation subsides. These two characteristics make NO levels an ideal biomarker for managing asthma status. For this reason, in 2011, the American Thoracic Society (ATS) issued new guidelines recommending the measurement of exhaled nitric oxide for the diagnosis and management of asthma. A diagnosis of asthma can be made when the concentration of nitric oxide in exhaled breath (fractional exhaled nitric oxide or FeNO) exceeds 50 ppb.

If a person is diagnosed with asthma, there is an effort to identify the irritant or combination of irritants that trigger the onset of asthma symptoms. Once the trigger is identified, the goal is to prevent the onset of symptoms by, e.g., avoiding the trigger and by properly using prescribed long-term control medications. In addition, patients are encouraged to develop an asthma action plan. The goal of an asthma action plan is patient self-management, e.g., the control and prevention of the onset of asthma symptoms. In general, asthma action plans are divided into three stages, labeled as the Green Zone, Yellow Zone, and Red Zone. In the Green Zone, the patient is doing well, with no symptoms, and the individual can engage in all usual activities and is advised to continue taking prescribed long-term control medicines such as inhaled corticosteroids. In the Yellow Zone, the patient is experiencing symptoms, but can do some, but not all, of the usual activities, and the patient is advised to take quick-relief medication. In the Red Zone, the individual is experiencing severe symptoms wherein quick-relief medications do not help and the patient is advised to seek immediate medical help. Examples of asthma action plans are available at http www.cdc.gov/asthma/action-plan.html.

Although asthma sufferers are encouraged to control triggers and develop action plans, it is estimated that less than half of asthma sufferers avoid triggers or follow action plans. In addition, avoiding triggers can be difficult. Information, for example, is generally available regarding some potential triggers. Government agencies around the world routinely monitor air pollutants in an attempt to warn populations of unhealthy conditions. For example, the U.S. Environmental Protection Agency monitors for major pollutants such as sulfur dioxide, carbon monoxide, particle pollution, and ground level ozone. (See, e.g., Air Quality Index: A Guide to Air Quality and Your Health at https://www3.epa.gov/airnow/aqi_brochure_02_14.pdf, U.S. Environmental Protection Agency Office of Air Quality Planning and Standards, Outreach and Information Division, Research Triangle Park, NC, February 2014 EPA-456/F-14-002). The data from the monitoring system is then used to generate an Air Quality Index (AQI) that employs a scale from 0 to 500, with scores above 100 being considered as unhealthy. Other organizations, such as the American Academy of Allergy Asthma & Immunology's National Allergy Bureau (http://www.aaaai.org/global/nab-pollen-counts) collects and reports on a regional basis pollen and mold spore levels collected by counting stations throughout the United States. However, while this information can be helpful in avoiding some triggers, the information is too general to provide information tailored to an individual's particular circumstances. In other words, such generalized information lacks the specificity on an individual basis for reliably predicting the onset of asthma symptoms.

Accordingly, it would be advantageous to increase the likelihood for successful preventive therapy to avoid the onset of asthma symptoms on an individual basis by integrating, for example, FeNO measurement technology with measured potential triggers geared to an individual's sensitivities and location. In addition, it would be advantageous to be able to correlate an individual's therapy responses and symptom onset prediction errors to improve the predictability of the onset of asthma symptoms for a particular individual's asthma status and for the environmental conditions at that individual's location.

BRIEF SUMMARY OF THE INVENTION

The present invention is a system and method of employing collected data for potential triggers and pertinent individual health data to predict the risk of the onset of asthma-related symptoms based on an individual's particular sensitivities to allow for preventive therapy tailored on an individual basis, and to revise the risk assessment criteria where a prediction error is encountered. Advantageously, the present asthma management system increases the ability of asthma sufferers to predict and manage the onset of asthma symptoms based on their location, asthma profile and status, and to continuously improve the accuracy of the asthma symptom onset prediction.

In one embodiment of the present invention, an asthma management system comprises at least one individual user interface and one or more environmental factor collection points in electrical communication with a computer system. The user interface is adapted to send and receive asthma-related information and data, including a user's asthma profile and real-time asthma status data to the computer system. The one or more environmental factor collection points are adapted to send and receive environmental data to the computer system. The computer system further comprises one or more processors connected to memory. The one or more processors are programmed with executable instructions for implementing one or more algorithms for (1) collecting and storing in memory data received from the individual user interface and from the environmental factor collection points, (2) aggregating the data received from the individual user interface and the environmental factor collection points, (3) implementing one or more algorithms to generate an asthma symptom onset prediction based on the aggregated data, and (4) communicating the asthma symptom prediction to the user interface. The one or more processors are further programed with executable instructions to revise the one or more asthma symptom onset prediction algorithms where the generated asthma onset prediction and the real-time asthma status data indicate a prediction error.

In another embodiment, one or more computer systems comprising one or more computer processors is connected to one or more computer databases (memory) that are in electrical communication with environmental factor data collection points and with individual user interfaces via a communication network. The environmental factor data and individual user pertinent health data is collected and aggregated via the network and the computer system. The computer processors are programmed with executable instructions to run predictive algorithms based on collected environmental factor data and personal health data to assess the risk of the onset of asthma symptoms in the individual user. The calculated risk assessment is then communicated to the individual user via the network to the user interface. In circumstances where the onset of asthma symptoms are communicated to the computer system where the predictive algorithms' calculated risk assessment indicate either no risk or a low risk of the onset of asthma symptoms (prediction error), the computer system updates the user's health profile and associated algorithms for the particular environmental factors and the individual's current health data culminating in the unpredicted onset of asthma symptoms, e.g., in a self-validating, continuous feedback loop.

In another embodiment, the individual user interface comprises a personal asthma management device that includes at least one processor connected to memory and programmed with executable instructions for collecting, storing, and updating a user's asthma profile, and a user's real-time data such as FeNO level status, and location, wherein the personal device is connected via a communication network such as the Internet, either via a wired or wireless connection, to a remotely located user database. The personal asthma management device can include a FeNO monitor as part of the device. The user's asthma profile, real-time data, such as FeNO level status, and location are communicated via the network to the user database. A second remotely located environmental factor database is adapted to store measurements of environmental factors, such as atmospheric particulate matter, collected from monitors or sensors from selected geographic regions or locations. One or more processors are connected to the user and environmental factor databases and programmed with executable instructions for performing at least the following: (1) comparing a user's asthma profile and status with the current environmental factors for the user's location and calculating an asthma symptom onset risk assessment, (2) communicating the symptom onset risk assessment prediction to a user's personal device, and (3) updating the user's asthma profile where a prediction error is encountered.

In another embodiment, an asthma management system comprises one or more third-party environmental collection points for collecting environmental factor data and one or more private environmental factor collection points for collecting environmental data and a cloud-based communication network in communication with the third-party and private environmental collection points. One or more location-aware personal communication devices are configured for communication with the cloud-based communication network, along with a computer system in communication with the cloud-based communication network.

In another embodiment, a FeNO monitor is in wired or wireless communication with one or more of the location-aware personal communication devices, allowing an individual user to input his or her FeNO level measurements from the FeNO monitor.

DETAILED DESCRIPTION OF THE INVENTION

As used herein, the terms "comprises," "comprising," "includes," "including," "has," "having," or any other variation thereof, are intended to cover a non-exclusive inclusion. For example, processes, methods, articles, or apparatuses that comprise a list of elements are not necessarily limited to only those elements but may include other elements not expressly listed or inherent to such processes, methods, articles, or apparatuses. Further, unless expressly stated to the contrary, "or" refers to an inclusive "or" but not to an exclusive "or." For example, a condition A or B is satisfied by any one of the following: A is true (or present) and B is false (or not present), A is false (or not present) and B is true (or present), and both A and B are true (or present).

Also, use of "a" or "an" are employed to describe the elements and components of the invention. This is done merely for convenience and to give a general sense of the invention. This description includes one or at least one and the singular also includes the plural unless it is obvious that it is meant otherwise.

Unless otherwise defined, technical and scientific terms used herein have the same meaning as commonly understood by one of ordinary skill in the art to which this invention belongs. Although methods that are similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, materials, methods, and examples are illustrative only and not intended to be limiting.

In the following description, numerous specific details, such as the identification of various system components, are provided to understand the embodiments of the invention. One skilled in the art will recognize, however, that embodiments of the invention can be practiced without one or more of the specific details, ordinary methods, components, materials, etc. In still other instances, well-known structures, materials, or operations are not shown or described in detail to avoid obscuring aspects of various embodiments of the invention.

Reference throughout this specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" in various places throughout this specification are not necessarily all referring to the same embodiment. Furthermore, the particular features, structures, or work characteristics may be combined in any suitable manner in one or more embodiments.

Figure 1:
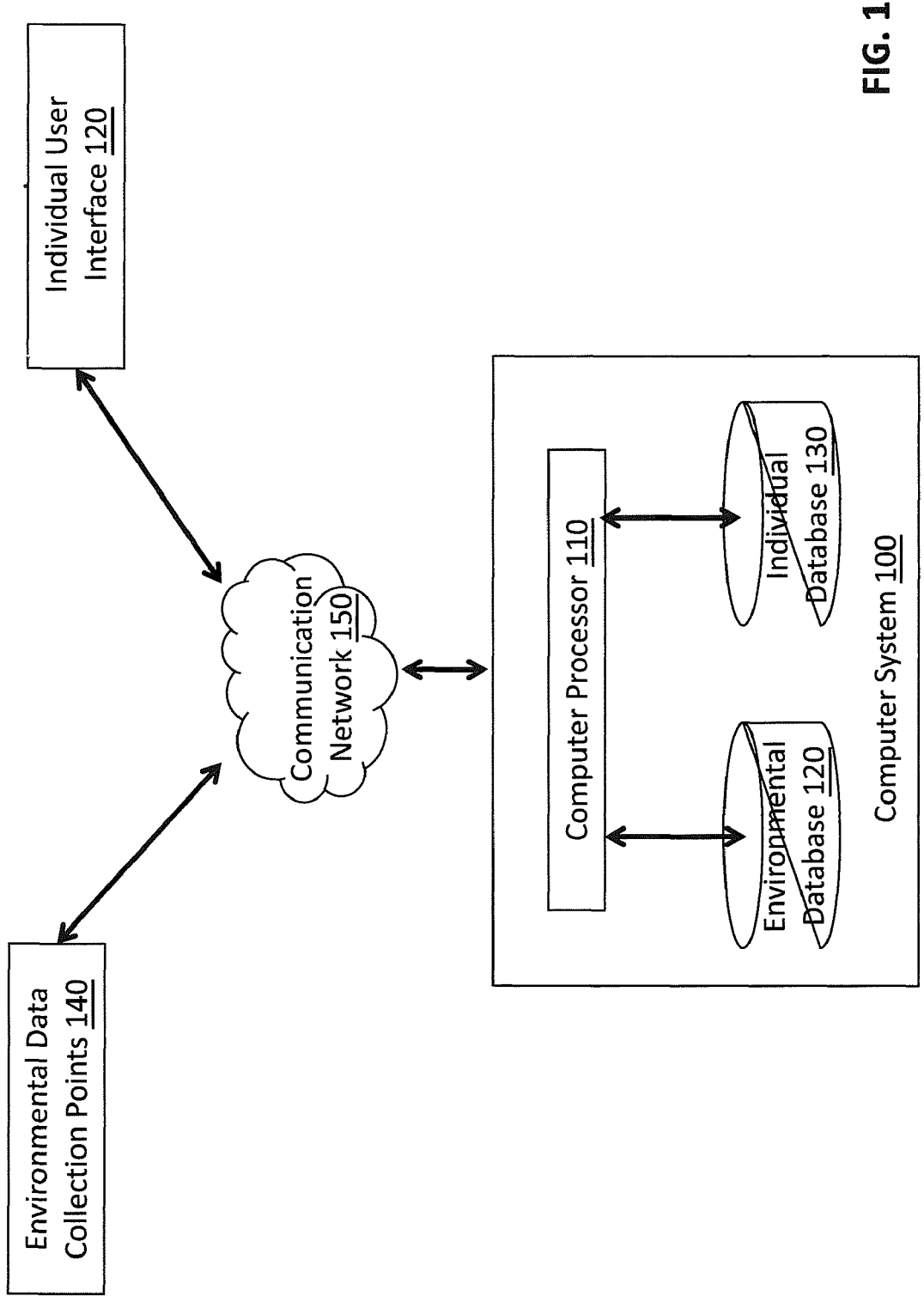
FIG. 1 is a block diagram illustrating one embodiment of an asthma management system.

Referring to FIG. 1, a block diagram illustrating one embodiment of the asthma management system of the present invention is shown. A computer system 100 includes one or more computer processors 110 connected to memory, e.g, as illustrated here an environmental database 120 and an individual database 130. The computer system is connected to environmental factor collection points 140 and to one or more individual user interfaces 120 via a communication network 150. Although illustrated here as separate components, the computer system, user interface, environmental factor collection points, and the communications network can be incorporated into a single device. For example, a single device can include a FeNO monitor (an example of one type of user interface), and a sensor for sensing particulate matter in the local environment, both of which are in electrical communication with a computer system within the device. Other aspects of these components are explained and illustrated more fully below.

For purposes of the present invention, the communication network is any electrical means for transmitting or communicating information and data between the environmental factor collection points, the individual user interface or interfaces, and the computer system. These can comprise, for example, wired or wireless means of electrical transmission, or a combination of wired or wireless transmission. While the particular communication system employed can include combinations of wired and wireless components, a particularly preferred embodiment of the present asthma management system includes wireless communication. Such systems can be composed of various wireless communication systems, including personal area networks such as Bluetooth®, cellular communications, WiFi networks, satellite communications and the like. In addition, a particularly preferred system for allowing a user to report and receive alerts is a cloud-based system, which can employ a variety of platforms, such as infrastructure as service (IaaS), platform as service (PaaS), software as service (SaaS), and the like.

The user interface allows a user to send and receive information to and from the computer system. This includes user specific data such as sensors that measure the properties of the user/asthma patient, as well as, for example, measurement devices like FeNO monitors and spirometers. The user interface can also include any device, including personal devices, that allows for a user to transmit and receive information via the communications network. Such personal devices include, for example, computers, mobile phones (e.g., smart phones), tablets, and the like. Preferably, such devices include the ability to provide the user's location (location-aware devices). In one embodiment, the user interface can include a FeNO monitor integrated into, or in wired or wireless communication with, a personal device. As an example, a user's smart phone and FeNO monitor can be connected via a Bluetooth® such that a user's FeNO measurements can be communicated to the user's smart phone for communication, along with any other pertinent user date, to the computer system.

In the embodiment illustrated, an individual user interface is adapted to send asthma-related data, including asthma profile data and real-time asthma status data to the computer system via the communication network. The asthma profile includes any asthma-related individual information. This can include, for example, self-reported asthma surveys that generate numeric results, such as symptom scores, a total score of self-reported symptoms that can be calculated from an asthma control score (ACT), an asthma control questionnaire (ACQ), or other similar surveys. In addition, the information can include genetic factor information, e.g., an assessment of genetic pre-disposition to severe outcomes due to asthma, which can be based on factors such as race, sex, age, weight, and family history. Measurements based on genetic factors can be based on scoring the likelihood of predisposition on a scale, for example, of between zero and ten. An individual's asthma status includes, for example, an individual's real-time asthma status, e.g., whether a person is presently in the green, yellow, or red zone, what medications are currently being taken by the individual, and the dosage, and measurements of FeNO levels, respiratory rate, airway obstruction (spirometry), heart rate (physical strain), activity level (accelerometer), asthma peek flow meter measurements, forced expiratory volumes (FEV1), and other pertinent measurements. The real-time asthma status can also include a person's physical status, e.g., whether a person is indoors or outdoors, whether a person is active (e.g. running, walking, bicycling) or sedentary, etc. In addition, the asthma status preferably includes a person's physical location. The user interface, in addition to providing to the computer system an individual's relevant asthma related data, the user interface permits the user to receive asthma related information from the computer system, such as a prediction of the onset of asthma symptoms. The user interface, of course, may include one or more components for transmitting data to and from the computer system. For example, the user interface may include a port for plugging in a FeNO monitor to input a user's FeNO levels, and a separate screen for receiving asthma symptom onset alerts.

Environmental factors include anything (alone or in combination) that can trigger asthma symptoms in an individual. Again referring to the illustration of FIG. 1, the environmental factor collection points are adapted to send and receive data to the computer system via the communication network, e.g., one or more environmental factor collection points are in electrical communication with the communication network wherein environmental factor data are transmitted to an environmental factor database via the communication network. Environmental factors include environmental factor data, which comprises measurements of things that can be potential triggers to the onset of asthma symptoms, and can also include localized weather data, e.g., current temperature, wind speed and direction, and precipitation events. The collection points can be third-party or private collection points, such as environmental sensors or monitors and the like. For example, the sensors or monitors can be public sensors, e.g., such as those employed in instrument housings used by the U.S. Environmental Protection Agency to measure major pollutants such as sulfur dioxide, carbon monoxide, particle pollution, and ground level ozone that are typically used to generate an Air Quality Index (AQI). In addition, many local agencies employ sensors or monitors to measure for pollutants or irritants such as nitric oxides (NOx), sulfur oxide (SOx), soot, and suspended particulate matter (e.g., PM1, PM2.5, and PM10, the numbers referring to the diameter of the particulate matter in micrometers). In addition, concentrations of many types of pollens and mold can be sensed. The measurements made by each of these public sensors are typically available via the Internet. In addition, private sensors/monitors can be employed to collect data on environmental factors, for example, in a building or home.

Again referring to FIG. 1, the computer processor or processors are programmed with executable instructions for collecting and storing in memory data received from the individual user interface and data from the environmental factor collection points, and aggregating the data received from the individual user interface and the data from the environmental factor collection points. In addition, the processor or processors are programed with executable instructions for implementing one or more predictive algorithms to generate an asthma symptom onset prediction based on the aggregated data. The processor or processors are further programmed with executable instructions to transmit or communicate the asthma symptom onset prediction to the individual user interface.

Once the aggregated environmental factors are correlated with an individual's asthma profile and asthma status, and, through one or more predictive algorithms, a risk assessment regarding the potential for the onset of asthma symptoms is then communicated to the individual user via the communication network, this actionable information can then be used by the individual to take, for example, additional medication to inhibit the onset of asthma symptoms. In addition, the processor is programmed with executable instructions to update a user's information and associated algorithms based on prediction error. A prediction error occurs where the predictive algorithm and the individual user's real-time asthma status are discordant. For example, the predictive algorithm may indicate a low risk for the onset of asthma symptoms for an individual based on the user's profile and status and the environmental factors for that user's location. Nevertheless, that user may experience asthma symptoms. The user's information is then updated to modify the predictive algorithm to take into account the particular combination of environmental factors and the user's asthma status in making future risk assessments. As additional prediction errors are encountered for a particular individual, the accuracy and reliability of the risk assessments for that individual will improve.

The environmental factors collected will preferably be as specific to the individual user's location as possible. The collection of measurements from public sensors/monitors can generally be collected from a user's general area, while private sensors can be located in user-specific areas, such as in the user's home. For example, a particular user may have a predisposition for the onset of asthma symptoms based on one specific type of irritant, such as smoke, and also to nitric oxides. Based on local publicly available measurements, there may be little or no smoke in the user's general area, but a change in wind speed and direction may indicate that the environmental factors for the user's location may change at a given time. As a further example, public sensors may not show sufficient levels of nitric oxide in the general environment to trigger the onset of asthma symptoms for a particular user, but the user's local monitor may show sufficiently high levels of nitric oxide in the user's immediate environment to trigger the development of symptoms. It is known that a rise in FeNO in a user's exhaled breath can predict the onset of asthma symptoms from two to seven days in advance of the development of symptoms. This alone can provide predicative power. However, the nitric oxide levels from a local monitor can extend the predicative power beyond seven days since it allows the user to be alerted to exposure to nitric oxide and an expected rise in the user's FeNO levels before they might become apparent from a user's FeNO measurements. Accordingly, action can be taken much farther in advance of the development of symptoms, such as taking medication to decrease the likelihood that symptoms will develop.

As discussed above, the computer processor is programmed with executable instructions for running predictive algorithms. Current expected symptoms can be expressed, for example, as a combination of the recent irritant levels and current spirometry values. It can also be expressed as a function of recent FeNO values, e.g., $\overline{Symptoms} = \amalg(E(U_{irr}), E(K_0), E(V_0))$, where $E(x)$ is a generalized average of a series x, such as an arithmetic mean, geometric mean, weighted average, integral, FIR, etc., and $\amalg(x, y, z, \ldots)$ is a linear, non-linear of other combination of x, y, z, etc. Current actual symptoms can be expressed as a function of a self-reported symptom score, e.g., $Symptoms = f(S_0)$.

In addition, based on analysis of prior data, an expected change in FeNO can be calculated from the combination of the expected change in air quality, e.g., $\Delta_F = \sqcup (U, \Delta_U)$. Then, based on analysis of how FeNO predicts symptoms, future expected symptoms can be computed as: FutureSymptoms=f(F,$\Delta_F$,Symptoms,Symptoms). Finally, it is possible to directly estimate future symptoms using current symptoms and forecasted air quality by modeling in two stages. First, the algorithm would be trained during a patient's initial course of therapy to model the predictive relationship of FeNO, and then the same model provided with updated training to reflect the effects of various parameters on FeNO while avoiding exposure to symptoms. This allows the algorithm to learn (grow smarter) without having to wait for symptoms to occur.

In geographical areas where many active users are present, the predicted symptoms for a particular user can also include crowd-sourced estimation terms generated by taking the local average change in symptoms from a recent time to the current time, and adding the delta to the given user's most recent symptoms.

In addition, the operators in this model can use various parameters that will be fixed for the total population, for subpopulations, and/or for individual users. The parameters themselves depend on a model of how various factors relate to the effect that the input values have on symptoms. These parameters can be established and modified over time in several ways. Seed values for a particular parameter for a particular user will be based on previously established values. They may be established at the population level, or for specific subpopulations based on genetic information, height, weight, age, etc. Seed values can be established using separate research, clinical studies, established standards, or from a self-developed dataset. Learned values for a particular parameter are refined over time using an interative loop. In the case where the parameters are simple weighting factors, the loop for predicted FeNO can take the form:

$$P'_k = \frac{F_{k+1}}{U_k}$$

$$P' = \frac{1}{K}\sum_{k=1}^{K} P'_k$$

In this case, the actual FeNO values divided by the air quality score for each measured point can be used to set the multiplier for the next prediction. An example of one such algorithm is one that sets the operator $\sqcup(x,y)$ as a weighted average of x and y.

Figure 2:
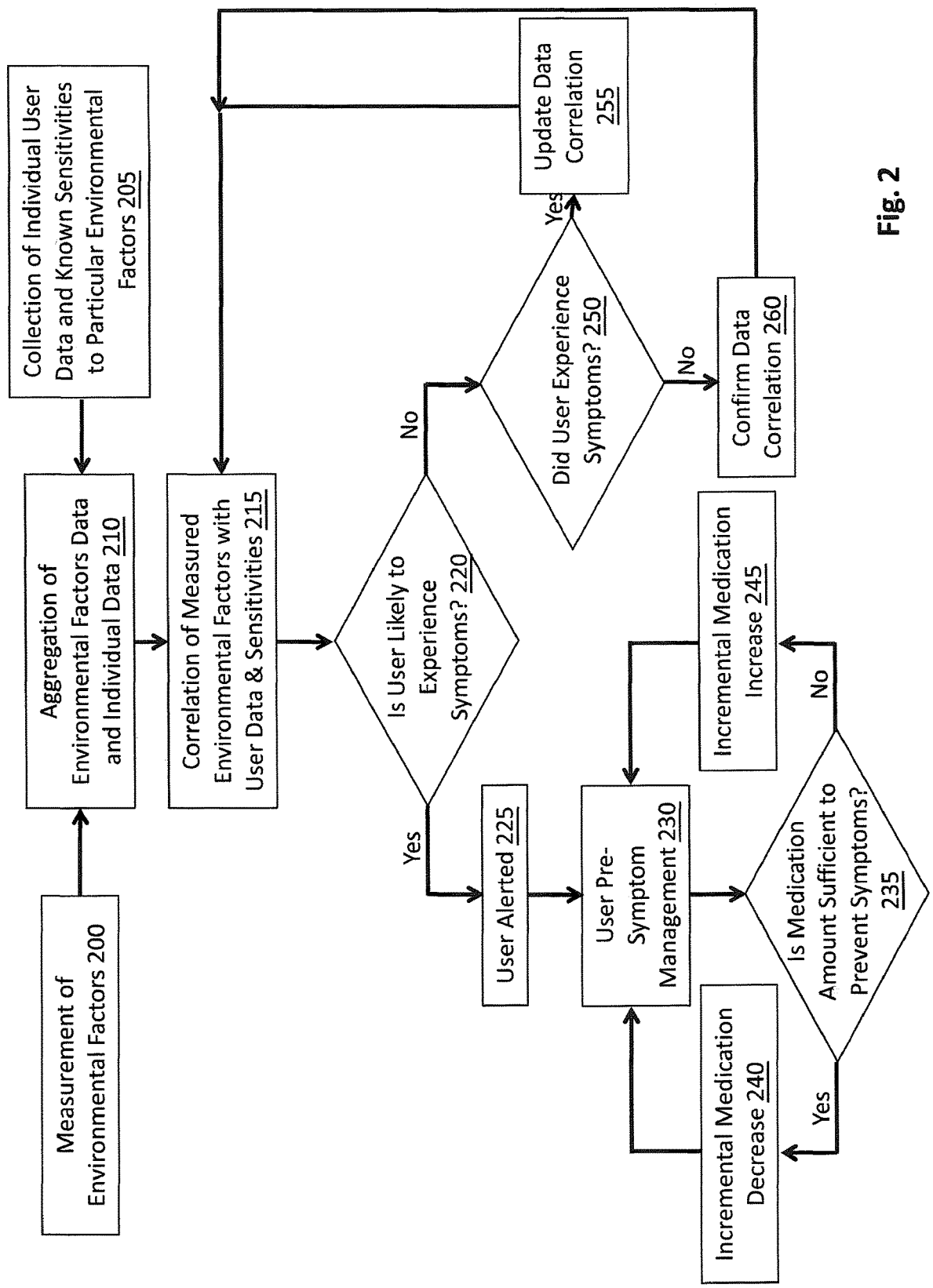
FIG. 2 is a flow diagram illustrating one embodiment of a method providing a user with actionable advice in an asthma management system.

Referring again to FIG. 1 and to the flow diagram of FIG. 2, the flow diagram illustrates one embodiment of the asthma management system of the present invention based upon the above predicative algorithms. The analysis begins with the measurement of environmental factors from environmental data collection points 140 (block 200) and the collection of individual user information input (block 205), such as communicated from the individual user interface 120. The environmental factors, which may be collected from several sources, e.g., from public and private sensors/monitors as discussed above, are aggregated (block 210) and stored in environmental database 120. The input of individual information is stored in individual database 130. A computer processor 110 is programmed to correlate the aggregated environmental information (block 215) with a user's individual data to determine whether a user is likely to experience symptoms (block 220). If so, the user will be alerted (block 225) via communication, for example, to the individual user interface 120.

It is contemplated that many users will have an asthma action plan, a plan developed generally with a patient's doctor. The action plan generally covers what medications to take, when to take them, and under what conditions additional treatment should be sought, e.g., a trip to the emergency room. For users with an asthma action plan, medication is managed based on a zone. Based on their level of control and symptoms, patients determine whether they are in a Green, Yellow, or Red zone. The plan will generally prescribe different medication regiments for each zone.

Thus, one action the present system can provide is the likelihood that a user will experience symptoms (block 220), and correlate them with a user's action plan, e.g., this model can be used to determine the user's action plan zone. In an ideal case, the output of the predictive model (trying to determine symptoms in the near future) will be used to assign the patient's zone, followed by the administration of the user's medication. In practice, it is often desirable under the user's pre-symptom management (block 230) to modify the asthma treatment in a way that enables the user to take the least amount of medication while avoiding the onset of any asthma-related symptoms. Thus, the user can provide feedback on whether the medication taken was sufficient to prevent the onset of symptoms (block 235). This feedback can indicate that a user's medication might be reduced. However, whenever a medication dosage is changed (or the medication itself is changed), there is often a period of trial-and-error to find the best medication and the best dosage. Currently, the process is largely based on symptoms. That is, the user may slowly increase the medication until symptoms disappear, or they may slowly decrease their medication until symptoms appear and then back off to the smallest effective dose (dosage titration).

The use of the present asthma management system to predict future symptoms can allow step-down dosage titration to be performed until symptoms are predicted, and then the dose can be stabilized before any symptoms occur. Accordingly, if the medication is sufficient to prevent symptoms (block 235), the system can provide for incremental medication decrease (block 240), or if not, then for an incremental medication increase (block 245).

The present system allows for increasing the reliability of the prediction of the onset of symptoms based on specific environmental factors and a user's own data. In addition to helping adjust the dosage of medication if the correlation process predicts it is likely that a user will experience symptoms, there may be occasions where based on the environmental factors and the user data, the system will decide that there should be no onset of symptoms (e.g., a user with an asthma plan is in the Green zone). If the prediction is that a user is unlikely to experience symptoms, the issue is whether the user did experience symptoms (block 250). If such a prediction error is encountered, the system allows for updating the user profile and associated algorithms for the conditions triggering the symptoms (block 255) to include the environmental factors giving rise the onset of symptoms. If not, the system allows for confirming that the data correlation is correct (block 260). Under this situation where a user's predicted symptoms are significantly different from his or her most recent self-reported symptoms, the system can alert them to the impending change via, for example, mobile phone alert, SMS, email, voice call, and the like. The user can then determine what, if any, action to take in advance of the change in symptoms.

Figure 3:
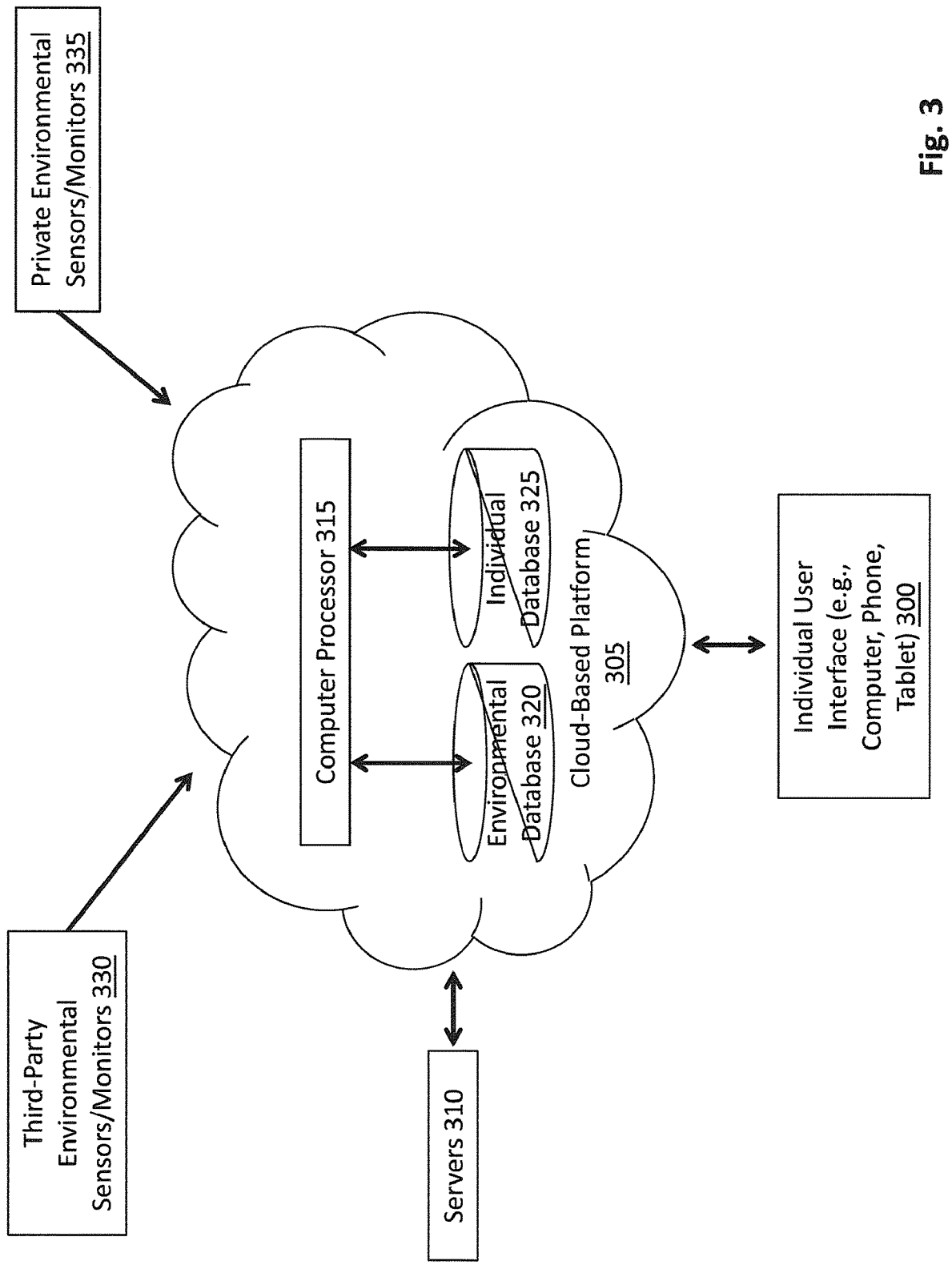
FIG. 3 is a block diagram illustrating an embodiment of an asthma management system implemented in a cloud-based environment.

Referring to FIG. 3, a cloud-based system is shown illustrating one embodiment of the present asthma management system. Employing preferably a location-aware personal device 300, e.g., a computer, tablet, or smart phone, a user opens an application that allows for communicating with a cloud-based platform 305 in communication with one or more servers 310 employing one or more computer processors 315 and including one or more environmental databases 320 and one or more individual databases 325. Using the location-aware personal device, location specific environmental data is obtained from one or more data collection points, such as third-party environmental sensors or monitors 330, e.g., air quality information such as AQI data, and private and/or user-owned monitors or sensors 335. In addition, user information is input into the user's personal device. Such user information includes, for example, a user's symptom score (e.g., self-reports from the user, manually triggered or via check-in). Such reports can be obtained from a mobile app, email, SMS, web form, or voice-assistant interaction. The symptom score can also be inferred from rescue medication usage, collected by self-reports or from connected inhalers. Other user information can include the input of the user's genetic factors, FeNo levels obtained from a user's own FeNO monitor, or monitors located at a point-of-care or other setting such as a pharmacy, an office or home peak flow meter, an office or home spirometer, and the like. Other user specific data can also be input via the user interface, such as spirometer data, heart rate, etc. Employing the collected data from third-party sensors, private sensors, and user-supplied data, the predictive algorithms are run and alerts are issued to the user, e.g., via the user interface.

Depending on usage, the algorithms could be run entirely on a user's personal device to compute predicted symptoms based on collected data. Local execution can be desired when locally gathered information forms the bulk of the model data. But, local execution is not always reliable if the purpose is to provide alerts, dose titration messages, or other interactions not initiated by the user. In those cases, the algorithm could be run on a server capable of generating a push notification, email, SMS, voice call, and the like, to the user interface, e.g., a user's personal device such as a smart phone.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with anyone or more of the features described herein. The breadth of the present invention is not to be limited by the subject specification, but rather only by the plain meaning of the claim terms employed.

This disclosure is sufficient to enable one of ordinary skill in the art to practice the invention, and provides the best mode of practicing the invention presently contemplated by the inventor. While a full and complete disclosure is made of specific embodiments of this invention, the invention is not limited by the exact construction, dimensional relationships, and operation shown and described. Various modifications, alternative constructions, design options, changes and equivalents will be readily apparent to those skilled in the art and may be employed, as suitable, without departing from the spirit and scope of the invention. Such changes might involve alternative materials, components, structural arrangements, sizes, shapes, forms, functions, operational features and the like.

What is claimed is:

1. An asthma management system, comprising:
    a. a location-aware personal communication device that includes a FeNO monitor for measuring the levels of nitric oxide in exhaled breath in communication with said location-aware personal communication device;
    b. one or more environmental factor collection points for measuring one or more potential asthma triggers;
    c. at least one computer system in electrical communication with said location-aware personal communication device and said environmental factor collection point, said location-aware personal communication device adapted to send and receive asthma-related data including asthma profile and real-time asthma status data including measurements of said level of nitric oxide in exhaled breath to said computer system, and said environmental factor collection point adapted to send and receive data as to said potential asthma triggers to said computer system; said computer system further comprising one or more processors connected to memory, said one or more processors programmed with executable instructions for implementing one or more algorithms for (1) collecting and storing in said memory data received from said location-aware personal communication device and from said environmental factor collection point, (2) aggregating said data received from said location-aware personal communication device and environmental factor collection point, (3) implementing one or more algorithms to generate an asthma symptom onset prediction based on said aggregated data including the level of nitric oxide in said exhaled breath and at least one of said potential asthma triggers collected from said environmental factor collection point, and (4) communicating said asthma symptom prediction to said location-aware personal communication device; and
    d. one or more processors further programed with executable instructions to revise said one or more asthma symptom onset prediction algorithms where said generated asthma onset prediction and said real-time asthma status data including the level of nitric oxide in said exhaled breath correlated to the presence of said one or more potential asthma triggers indicate a prediction error when said generated asthma onset prediction and said real-time asthma status data are discordant.

2. The asthma management system of claim 1 wherein one or more environmental factor collection points for measuring one or more potential asthma triggers includes a nitric oxide monitor.

3. The asthma management system of claim 1 wherein said real-time asthma status data includes real-time asthma medication dosage.

4. The asthma management system of claim 3 wherein said one or more processors are further programmed with executable instructions for implementing one or more algorithms for communicating incremental medication increases or decreases to said location aware personal communication device in response to said real-time asthma medication dosage.

5. The asthma management system of claim 1 wherein said asthma symptom onset prediction algorithm includes crowd-sourced data.

6. The asthma management system of claim 1 wherein said asthma symptom prediction communicated to said location aware personal communication device is correlated to an asthma action plan.

\* \* \* \* \*